(12) United States Patent
Plumptre et al.

(10) Patent No.: US 8,986,261 B2
(45) Date of Patent: Mar. 24, 2015

(54) DRUG DELIVERY DEVICE

(75) Inventors: David Aubrey Plumptre, Worcestershire (GB); Christopher James Smith, Holmes Chapel (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/005,879

(22) PCT Filed: Mar. 22, 2012

(86) PCT No.: PCT/EP2012/055056
§ 371 (c)(1),
(2), (4) Date: Sep. 18, 2013

(87) PCT Pub. No.: WO2012/130704
PCT Pub. Date: Oct. 4, 2012

(65) Prior Publication Data
US 2014/0012208 A1    Jan. 9, 2014

(30) Foreign Application Priority Data

Mar. 25, 2011   (EP) .................................... 11159757

(51) Int. Cl.
*A61M 5/315* (2006.01)
*A61M 5/24* (2006.01)
*A61M 5/31* (2006.01)

(52) U.S. Cl.
CPC ....... *A61M 5/31528* (2013.01); *A61M 5/31543* (2013.01); *A61M 5/24* (2013.01); *A61M 5/3146* (2013.01); *A61M 5/31573* (2013.01); *A61M2005/2488* (2013.01); *A61M 2005/3142* (2013.01); *A61M 2005/3152* (2013.01); *A61M 2205/581* (2013.01); *A61M 2205/582* (2013.01)
USPC ........................... 604/211; 604/207; 604/208

(58) Field of Classification Search
CPC .............. A61M 5/24; A61M 5/31543; A61M 2005/2485; A61M 5/31551; A61M 5/31528
USPC ......... 604/207, 208, 209, 210, 211, 232, 233, 604/234, 235; 403/348, 349
See application file for complete search history.

(56) References Cited

U.S. PATENT DOCUMENTS 6,679,647 B2 * 1/2004 Hixon ........................... 403/349
7,021,817 B2 * 4/2006 Huang et al. .................. 366/331

(Continued)

FOREIGN PATENT DOCUMENTS

| GB | 2155985 | 10/1985 |
|---|---|---|
| WO | 2008/074897 | 6/2008 |
| WO | 2010/139640 | 12/2010 |

OTHER PUBLICATIONS

International Search Report for Int. App. No. PCT/EP2012/055056, completed Jun. 4, 2012.

*Primary Examiner* — Nicholas Lucchesi
*Assistant Examiner* — Anh Bui
(74) *Attorney, Agent, or Firm* — McDonnell Boehnen Hulbert & Berghoff LLP

(57) ABSTRACT

A resettable drug delivery device includes a body, a cartridge holder for receiving a cartridge, and a releasable coupling connecting the cartridge holder to the body or the dose setting mechanism. During an initial rotational coupling movement of the cartridge holder relative to the body or the dose setting mechanism the cartridge holder is caused to move in a first axial direction relative to the body or the dose setting mechanism and during a continued rotational coupling movement of the cartridge holder relative to the body or the dose setting mechanism the cartridge holder is caused to move in a second, contrary axial direction.

16 Claims, 2 Drawing Sheets

(56) References Cited

U.S. PATENT DOCUMENTS

| | | |
|---|---|---|
| 7,585,126 B2 * | 9/2009 | Ling et al. .................. 403/359.4 |
| 2009/0254035 A1 * | 10/2009 | Kohlbrenner et al. ........ 604/135 |
| 2010/0324496 A1 * | 12/2010 | Plumptre et al. .............. 604/207 |
| 2011/0046566 A1 * | 2/2011 | Elahi et al. .................... 604/214 |
| 2013/0090602 A1 * | 4/2013 | Avery et al. ................... 604/189 |

\* cited by examiner

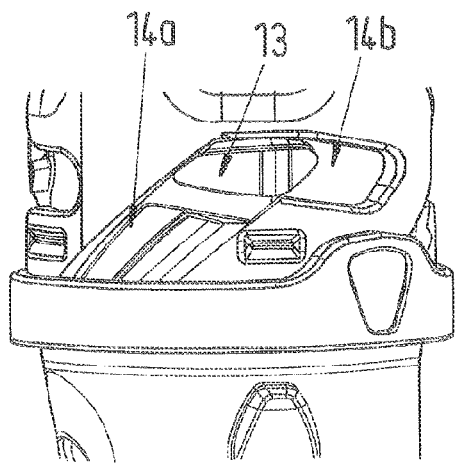
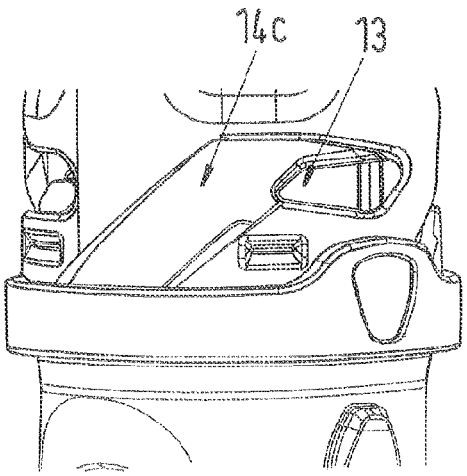
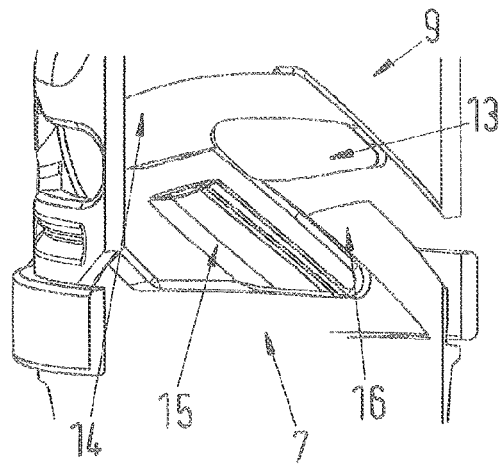
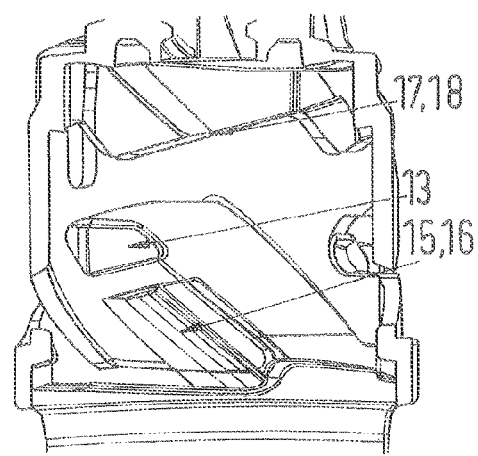

DRUG DELIVERY DEVICE

CROSS REFERENCE TO RELATED APPLICATIONS

The present application is a U.S. National Phase Application pursuant to 35 U.S.C. §371 of International Application No. PCT/EP2012/055056 filed Mar. 22, 2012, which claims priority to European Patent Application No. 11159757.1 filed Mar. 25, 2011. The entire disclosure contents of these applications are herewith incorporated by reference into the present application.

TECHNICAL FIELD

The present invention is directed to a drug delivery device, like a pen-type injector, that provides for administration by injection of medicinal products from a multidose cartridge. The device comprises a dose setting mechanism which may have a housing, a dose setting member (number sleeve), a drive member (drive sleeve), a clutch and a clicker.

BACKGROUND

There are basically two types of pen type delivery devices: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section with a dose setting mechanism connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The dosing section or dose setting mechanism is typically the portion of the pen device that is used to set a dose. During an injection, a spindle contained within the dose setting mechanism advances and presses against the bung or stopper of the cartridge. This force causes the bung or stopper to advance, in turn causing the medication contained within the cartridge to be injected through an attached needle assembly.

Different types of pen delivery devices, including disposable (i.e., non-resettable) and reusable (i.e., resettable) varieties, have evolved over the years. For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

In contrast to typical disposable pen type devices, typical reusable pen delivery devices feature essentially two main reusable components: a cartridge holder and a dose setting mechanism. After a cartridge is inserted into the cartridge holder, this cartridge holder is attached to the dose setting mechanism. The user uses the dose setting mechanism to select a dose. Before the user injects the set dose, a replaceable double-ended needle assembly is attached to the cartridge housing.

This needle assembly may be threaded onto or pushed onto (i.e., snapped onto) a distal end of the cartridge housing. In this manner, a double ended needle mounted on the needle assembly penetrated through a pierceable seal at a distal end of the cartridge. After an injection, the needle assembly is removed and discarded. After the insulin in the cartridge has been exhausted, the user detaches the cartridge housing from the dose setting mechanism. The user can then remove the empty cartridge from the cartridge retainer and replace the empty cartridge with a new (filled) cartridge.

Aside from replacing the empty cartridge with a new cartridge, the user must somehow prepare the dose setting mechanism for a new cartridge: the dose setting mechanism must be reset to a starting or initial position. For example, in certain typical resettable devices, in order to reset the dose setting mechanism, the spindle (piston rod) that advances in a distal direction during dose injection must somehow be retracted back proximally into the dose setting mechanism. Certain known methods of retracting this spindle back into the dose setting mechanism to a restart or an initial position are known in the art. As just one example, known reset mechanisms require a user to turn back (i.e. screw or rotate) or push back (retract) the spindle or some other portion of the dose setting mechanism.

Resetting of known dose setting mechanisms have certain perceived disadvantages. One perceived disadvantage is that such resettable devices use a large number of component parts, such resettable devices tend to be large and bulky, and therefore not easy to carry around or easy to conceal. Another disadvantage may be seen in a priming step required prior to the first use of the new cartridge.

SUMMARY

It is an object of the present invention to provide an improved resetting mechanism for a reusable drug delivery device.

This is obtained by a dose setting mechanism as defined in claim 1. The present invention is based upon a resetting mechanism that uses the initial proximal movement of the piston rod (spindle) at the start of the resetting procedure to decouple the dose setting mechanism, e.g. the driver, in order to permit the remainder of the resetting procedure to be completed. At the end of this resetting procedure, the dose setting mechanism, e.g. its driver, must be fully re-coupled in order to ensure that the device works accurately if the user dials and dispenses the first dose from the new cartridge without priming. To re-couple the dose setting mechanism, e.g. the driver, at the end of the resetting procedure the piston rod must be allowed to advance distally by a short distance out of the mechanism, i.e. the reverse of the proximal movement at the start of the resetting procedure. Because the device can be reset using the cartridge bung pressing on the piston rod during attachment of the cartridge holder to the dose setting mechanism there is potentially no space between the cartridge bung and the piston rod that would allow the distal movement of the piston rod to re-engage the dose setting mechanism. Therefore, at the end of the resetting procedure the cartridge bung and hence cartridge holder must be 'backed-off' slightly to allow the piston rod to advance distally as mentioned above.

A drug delivery device according to the present invention comprises a body, the body at least partially encasing components of a resettable dose setting mechanism, a cartridge holder for receiving a cartridge containing at least one medicinal product, and means for releasably coupling the cartridge holder to the body or the dose setting mechanism.

Preferably said means are adapted and arranged such that an initial rotational coupling movement of the cartridge holder relative to at least one of the body and the dose setting mechanism causes the cartridge holder to move in a first axial direction relative to the body and/or the dose setting mechanism and that a continued rotational coupling movement of the cartridge holder relative to the body and/or the dose setting mechanism causes the cartridge holder to move in a second axial direction, which is contrary to the first axial direction, relative to the body and/or the dose setting mechanism. The first axial direction is typically contrary to the distal direction the piston or bung moves within the cartridge during dispensing, i.e. the first axial direction is typically the proximal direction.

According to a first embodiment, the means for releasably coupling the cartridge holder to the body and/or the dose setting mechanism comprise at least one lug and a corresponding groove for receiving and guiding the lug and for effecting the relative axial movements of the cartridge holder and the body and/or the dose setting mechanism upon relative rotation between the cartridge holder and the body and/or the dose setting mechanism. In other words, the groove defines a track or path in which the lug slides thus translating a rotation into rotatory and translatory components. For this first embodiment, there are different options how the lug and the groove may be provided to guide the cartridge holder. It may be sufficient to guide the lug in the groove such that only one face of the lug contacts one of the side walls of the respective groove. As an alternative, opposite faces of the lug may be guided within the groove, i.e. like a sliding block.

The present invention is not limited to the above-mentioned embodiment. Different ways are possible to allow the piston rod during re-coupling of the mechanism to advance distally by a short distance out of the mechanism, i.e. the reverse of the proximal movement at the start of the resetting procedure. As an alternative to the above-mentioned embodiment using lugs and grooves, the means for releasably coupling the cartridge holder to the body may comprise corresponding pairs of ramps or helical features provided on respective front faces of the body and cartridge holder to move the cartridge holder in the second axial direction relative to the body or the dose setting mechanism. Preferably, at least four pairs of corresponding ramps or helical features are provided on respective front faces of the body and cartridge holder. An advantage of not having lugs in grooves is that when tolerances are allowed for the lugs will also be slightly loose. Having separate helical ramps placed further from the lugs to some extent allows the plastic to flex slightly to accommodate slight interference enabling to design the nominal condition to have a tight fit. Also these helical ramps on the cartridge holder may be formed on a separate part of the mould tooling (ejector sleeve) and the position or length of this sleeve can be adjusted in the tool so that the distance from these helical ramps to the lugs on the cartridge holder matches the equivalent distance between the aperture and helical ramps on the inner body.

As a further alternative, a slot may be provided, e.g. in the body, guiding a tongue of the cartridge holder. The latter embodiment has the benefit of the tongue being visible from outside of the body thus allowing a user to see whether or not the cartridge holder is correctly attached to the body.

Further, the means for releasably coupling the cartridge holder to the body and/or the dose setting mechanism may comprise corresponding bayonet features formed on the cartridge holder and the body or the dose setting mechanism, respectively. Preferably, the means for releasably coupling the cartridge holder to the body and/or the dose setting mechanism comprise a bayonet lug formed on the cartridge holder and a groove formed on or in the body or the dose setting mechanism.

According to one aspect of the present invention, the means for releasably coupling the cartridge holder to the body and/or the dose setting mechanism comprise a groove having a first helical section with a first pitch and a second helical section with a second pitch, with the first pitch being contrary to the second pitch. In other words, if a lug or the like is moved within the groove, the lug moves upon rotation in a first axial direction when being guided in the first section and moves in the opposite (second) axial direction when being guided in the second section.

Preferably, the first helical section and the second helical section have a different lead, i.e. the component of the axial movement of the combined rotator and translator movement is larger in one of the section, preferably in the first section.

In addition, a third section of the groove may be provided between the first helical section and the second helical section with the third section having a lead differing from the leads of the first helical section and the second helical section.

According to a further embodiment, the drug delivery device further comprises means for releasably rotationally fixing the cartridge holder to the body and/or the dose setting mechanism. This prevents an unintended de-coupling of the cartridge holder from the body and/or the dose setting mechanism. Typically, said means comprise catching or snap-in means. Thus, the user may have to overcome a resistance for fully coupling the cartridge holder to the body and/or the dose setting mechanism. This provides for an audible and/or tactile feedback indicating that the cartridge holder is attached to the body and/or the dose setting mechanism.

Preferably, the means for releasably rotationally fixing the cartridge holder to the body and/or the dose setting mechanism comprise corresponding detent features provided on the cartridge holder and the body and/or the dose setting mechanism, respectively.

A compact and yet easy to handle drug delivery device may be provided, if the dose setting mechanism comprises a piston rod and a driver, wherein the driver has two driver components which are rotationally coupled to each other during dose setting and dose dispensing and which are rotationally de-coupled from each other during resetting of the dose setting mechanism.

According to a preferred embodiment of this idea, a clutch may be provided for rotationally coupling and de-coupling the two driver components, wherein de-coupling of the two driver components requires a relative axial movement between the two driver components. Further, a spring means may be provided biasing the two driver components to couple, wherein the spring force may be overcome when a proximal force is applied to the piston rod, causing the driver components to de-couple. Thus, the spring means will tend to cause the driver components to automatically re-couple when the proximal force is removed from the piston rod.

According to another embodiment, a spring means may be provided biasing the two driver components to de-couple, wherein the cartridge holder causes the two driver components to couple if the cartridge holder is coupled or fully attached to the body and/or the dose setting mechanism. Thus, the driver components automatically couple when the cartridge holder is attached to the body and/or the dose setting mechanism.

Preferably the movement of the cartridge holder in the second axial direction is significant, i.e. greater than e.g. 0.2 mm, so as to ensure that the drive mechanism can re-couple after reset.

BRIEF DESCRIPTION OF THE FIGURES

In the following, the invention will be described by a way of an example and with reference to the schematic drawings in which:

FIG. 4 shows the device fully reset axially prior to the cartridge holder back off, FIG. 5 shows the device reset and the cartridge holder backed off, FIG. 6 shows a view from inside during assembly of the cartridge holder to the housing component, FIG. 7 shows a view from inside with the components in their final locked position after back off.

DETAILED DESCRIPTION

Figure 1:
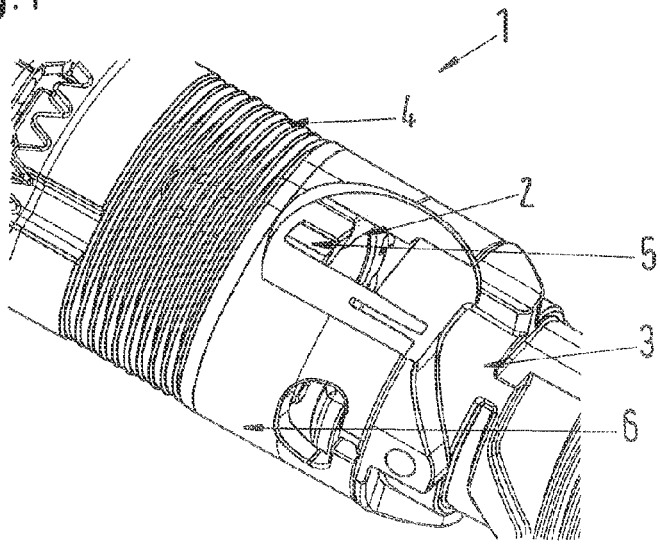
FIG. 1 shows a side view of the driver of a drug delivery device.

The drug delivery device 1 according to the present invention comprises a drive sleeve having two components, a rear (proximal) half 2 and a front (distal) half 3. Further, a coupling mechanism is provided for coupling and de-coupling the two halves of the drive sleeve in rotation. This coupling mechanism is effectively a clutch which may be engaged under the action of a spring 4, but which can be disengaged if the front half 3 of the drive sleeve is moved towards the rear half 2, compressing the spring 4 and de-coupling teeth 5 on the rear half 2 of the drive sleeve from corresponding tooth features on a coupling component 6. Coupling component 6 is fixed axially and rotationally, by means of snap features and guiding splines respectively, to the front half 3 of the drive sleeve, causing the two components 3, 6 to effectively behave as a single component, hereafter 3. In the example shown in FIG. 1, the spring 4 is designed as a wave spring.

FIG. 1 shows the drive sleeve halves 2, 3 in a coupled state, with the spring 4 essentially uncompressed (save for a small amount of compression applying a biasing force to the drive sleeve coupling clutch) and the teeth 5 on the rear half 2 of the drive sleeve engaged with the teeth on the inside of the coupling component 6.

Figure 2:
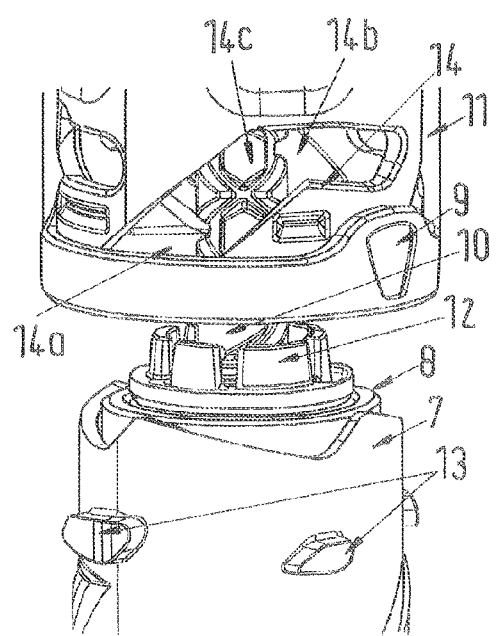
FIG. 2 shows a side view of the cartridge holder during resetting and prior to its attachment to a housing component.

FIG. 2 shows the cartridge holder 7 with a fresh cartridge 8 during resetting and prior to its attachment to a housing component 9, e.g. an inner body of the device. Further, a piston rod 10 is shown with one end protruding from the housing component 9. An outer body 11 which is a further housing component is shown surrounding an end of the inner body 9. The inner body 9 and/or the outer body 11 may encase a dose setting mechanism of the drug delivery device 1, i.e. the two components 2, 3 of the drive sleeve, the piston rod 10 and further components, like e.g. a dose dial sleeve and/or a clutch.

During device reset, when the cartridge is changed, the clutch is de-coupled by pressing proximally on the piston rod 10 shown in FIG. 2 by using for example a finger or preferably the bung of the new cartridge 8 as it is attached to the mechanism. The piston rod 10 engages with the front end 3 of the drive sleeve via a helical thread form, and the rear end 2 of the drive sleeve is fixed rotationally and axially relative to the mechanism during reset. Therefore as the piston rod 10 is pressed into the device the front end of the drive sleeve 3 is axially translated in the proximal direction and the clutch teeth 5 of the drive sleeve rear 2 initially preventing rotation of the drive sleeve front 3 and coupling component 6. Once the proximal movement of the drive sleeve front 3 and coupling component 6 is sufficient to decouple the clutch teeth 5 then the front half 3 of the drive sleeve and the coupling component 6, driven by the helical thread on the piston rod 10, are caused to rotate relative to the rear half 2 of the drive sleeve and spring 4 so as to allow the piston rod 10 to be pressed back into the device further. FIG. 2 shows an embodiment of the mechanism where the piston rod 10 rotates during both resetting and dose delivery and therefore has a bearing 12 attached on its end face to abut the cartridge bung (not shown).

When the cartridge 8 and hence piston rod 10 has been inserted into the mechanism as far as it can go, the cartridge holder 7 must be locked off to hold the cartridge 8 in position. This is achieved using a bayonet type connection, whereby after essentially axial motion of the cartridge holder 7 relative to the mechanism, the cartridge holder 7 is rotated to lock it into position against the housing component 9, 11. However it is a requirement of the device that at the end of resetting, the two halves 2, 3 of the drive sleeve are re-engaged, as shown in FIG. 1, during attachment of the cartridge holder 7. This is to ensure that if the user then takes the device 1 and dials and dispenses a dose without first priming the cartridge 8, then the dose they receive will be inside the ISO 11608-1 limits for dose accuracy. If the two halves of the drive sleeve 2, 3 are not re-engaged after the resetting procedure then the proximal distance moved by the drive sleeve front 3 in order to decouple clutch teeth 5 will be reversed during the delivery of the first dose following resetting, causing a corresponding advance of the piston rod which will deliver a small amount of drug in addition to the dose set by the user.

During reset, and if the user uses the cartridge bung to apply force to the piston rod, when the piston rod 10 reaches its maximum proximal position the cartridge bung and the bearing 12 on the end of the piston rod 10 will be in contact. In this case the piston rod 10, and therefore the drive sleeve front 3 which is threaded to the piston rod 10, cannot advance in the distal direction and therefore the drive sleeve halves 3, 6 cannot re-engage. In this case the re-engagement of the drive sleeve halves 2, 3 at the end of reset can only be achieved by moving the cartridge holder 7 and hence cartridge 8 back away from of the mechanism by an amount that enables the drive sleeve front 3, biased by action of the spring 4, to move axially away from drive sleeve rear 2 to allow the clutch teeth 5 to re-engage. This reverse motion of the cartridge holder 7 is referred to from now on as 'back off' and is essentially an axial movement in the opposite direction to attachment of the cartridge holder 7 during resetting of the device (i.e. the distal direction).

This 'back off' is achieved by providing bayonet features comprising bayonet lugs 13 formed on the cartridge holder 7 and corresponding bayonet grooves 14 (slots) which are formed on or in the inner body 9. The bayonet lugs 13 and the bayonet grooves 14 constitute means for releasably coupling the cartridge holder 10 to the body 9, 11 or the dose setting mechanism. Groove 14 has a first helical section 14a having a first pitch (to the upper right in FIG. 2) and a second helical section 14b having a second, opposite pitch (to the lower right in FIG. 2). In addition to the first pitch being contrary to the second pitch, the first helical section 14a and the second helical section 14b have a different lead as the first helical section 14a is steeper compared to the second helical section 14b. Optionally, a third section 14c of the groove 14 is provided interposed between the first helical section 14a and the second helical section 14b. This third section 14c has substantially no lead or a small lead. Hence, as a lug 13 travels within a groove 14, the cartridge holder 7 and the body 9, 11 move towards each other when the lug 13 is guided within the first helical section 14a, the cartridge holder 7 and the body 9, 11 rotate with substantially no relative axial movement when the lug 13 is guided within the third section 14c, and the cartridge holder 7 and the body 9, 11 move away from each other when the lug 13 is guided within the second helical section 14b.

In addition or as an alternative to the design of the grooves 14 having at least a first and a second section with a different pitch, the 'back off' is achieved by the helical ramp-like features 17, 18 depicted in FIG. 7. Hence, it is not necessary that the lugs 13 are in contact with the inclined walls of the respective second helical sections 14b to guide the lugs. Thus, as an alternative to the second helical sections 14b, a clearance may be provided allowing the lugs 13 to travel in the distal direction during the 'back off' step at the end of the rotation.

The lugs 13 may have a trapezoidal form adapted to the lead of the first and/or second helical sections as shown in FIGS. 2 to 7 to improve guidance in the groove 14. Further, one side face of the lug 13 may be adapted to the end wall of the second helical section 14b thus forming an abutment or stop face at the end of groove 14.

Figure 3:
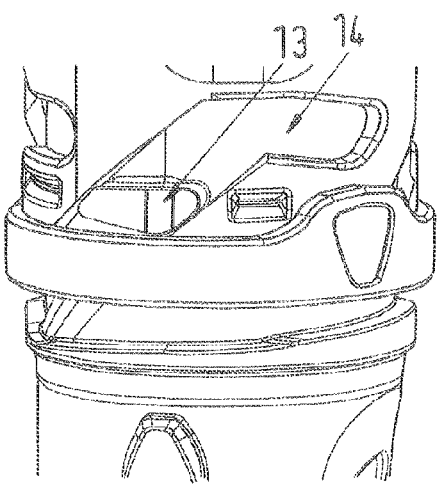
FIG. 3 shows the cartridge holder beginning to engage with the housing component.

FIG. 3 to FIG. 5 illustrate the sequence of events during the attachment of the cartridge holder 7 to the inner body 9. FIG. 3 shows a position of the cartridge holder 7 and the inner body 9 where the lugs 13 on cartridge holder 7 begin to engage with inner body bayonet features 14. In FIG. 4 the device is fully reset axially prior to 'back off' (at this point the drive sleeve clutch teeth 5 would be disengaged). FIG. 5 shows the device reset and 'backed off' with the bayonet features fully attached (at this point the drive sleeve clutch teeth 5 would be re-engaged as shown in FIG. 1). FIGS. 4 and 5 show how the lug 13 on the cartridge holder 7 slides down a slope within groove 14 that allows it to 'back off' by 0.5 mm. This 'back off' enables the reset clutch to re-engage as shown in FIG. 1. This is possible because as the cartridge holder 7 is 'backed off' by 0.5 mm, thus allowing the piston rod 10 and its bearing 12 to advance 0.5 mm.

In this device, due to the interaction between the piston rod 10, the inner body 9 and the front half 3 of the drive sleeve, there is a gearing ratio between the axial movement of the piston rod and the axial movement of the front half of the drive sleeve 3. In this embodiment the 0.5 mm distal movement of the piston rod 10 causes a greater distal movement of 1.0 mm of the front half 3 of the drive sleeve away from the rear half 2 of the drive sleeve which is sufficient to fully re-engage the reset clutch under the biasing force of the spring 4.

FIGS. 6 and 7 illustrate the same sequence of reset operation viewed from inside the device with the parts sectioned. These figures highlight helical features 17 on the end face 9a of the inner body 9 (and corresponding features 18 on the end face 7a of the cartridge holder 7) that help to guide the cartridge holder 7 during 'back off' and support the cartridge holder 7 when fully attached by reacting axial force from end face 7a of cartridge holder 7. Helical features 17, 18 may be designed as corresponding ramps provided between end faces 7a and 9a of inner body 9 and cartridge holder 7 to ensure that the bayonet lug 13 follows the "back off" slope with minimal axial play. Preferably, four or more pairs of corresponding ramps 17, 18 are provided. Further, (detent) features 15, 16 on the inner body 9 and cartridge holder 7 respectively, for releasably rotationally fixing the cartridge holder 7 to the body 9, 11 or the dose setting mechanism are depicted.

In FIG. 6 the device is shown during reset with the cartridge holder 7 initially assembled axially into the inner body 9 and when the bayonet lugs 13 on the cartridge holder 7 engage with slots 14 in the inner body. Thus, the cartridge holder 7 is guided to take a helical path upon relative rotation of the cartridge holder 7 and the inner body 9.

Detent features 15, 16 are provided on the cartridge holder 7 and the inner body 9, respectively. The detent features 15, 16 may "snap in" or align when the cartridge holder 7 is fully rotated in its final locking position in the inner body 9. This prevents an unintended de-coupling of the cartridge holder 7 from the body 9, 11 and/or the dose setting mechanism. The detent features 15, 16 depicted in FIGS. 6 and 7 work like catching or snap-in means. Thus, the user has to overcome a resistance for fully coupling the cartridge holder 7 to the body 9, 11 and/or the dose setting mechanism. This provides for an audible and/or tactile feedback indicating that the cartridge holder 7 is correctly attached to the body 9, 11 and/or the dose setting mechanism.

As shown in FIG. 6, the detent features 15, 16 are clear of each other but are just about to start engagement when the lug 13 is within the first helical section 14a or the third section 14c of the groove 14. In FIG. 7 the bayonet features 13, 14 are in their final position and the detent features 15, 16 are in their final detent position, too. Thus, all parts are in their final locked position after 'back off'. The device 1 is reset and ready to be used even without priming. However, a priming step may still be required or advisable for other reasons such as checking that the needle is not blocked and that the pen mechanism is working etc. Thus, the user should now prime the device to ensure that it is operating correctly and safely. However, in the event that the user does not prime the device before use (either user forgets to prime or deliberately omits the priming step) the 'back-off' of the cartridge holder should still ensure that the first dose received is within the ISO-11608 specified limits for dose accuracy.

The terms "medicament" or "medicinal product", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while β and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains β and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A drug delivery device, having a body, the body comprising a resettable dose setting mechanism, a cartridge holder for receiving a cartridge containing at least one medicinal product, and a releasable coupling connecting the cartridge holder to the body or the dose setting mechanism, wherein the releasable coupling is adapted and arranged such that an initial rotational coupling movement in a rotating direction of the cartridge holder relative to the body or the dose setting mechanism causes the cartridge holder to move in a first axial direction relative to the body or the dose setting mechanism and that a continued rotational coupling movement in the rotating direction of the cartridge holder relative to the body or the dose setting mechanism causes the cartridge holder to move in a second axial direction, which is in an opposite direction compared to the first axial direction, relative to the body or the dose setting mechanism,
   wherein the releasable coupling further comprises corresponding pairs of ramps or helical features provided on respective end faces of the body and cartridge holder to move the cartridge holder in the second axial direction relative to the body or the dose setting mechanism.

2. The drug delivery device according to claim 1, characterized in that the releasable coupling comprises at least one lug and a corresponding groove or slot for receiving and guiding the lug and for effecting the movement of the cartridge holder in the first and second axial directions upon relative rotation between the cartridge holder and the body or the dose setting mechanism.

3. The drug delivery device according to claim 1, characterized in that the releasable coupling comprises corresponding bayonet features formed on the cartridge holder and the body or the dose setting mechanism, respectively.

4. The drug delivery device according to claim 1, characterized in that the releasable coupling comprises a bayonet lug formed on the cartridge holder and a groove or slot formed on or in the body or the dose setting mechanism.

5. The drug delivery device according to claim 1, characterized in that the releasable coupling comprises a groove or slot having a first helical section having a first pitch and a second helical section having a second pitch, with the first pitch being contrary to the second pitch.

6. The drug delivery device according to claim 5, characterized in that the first helical section and the second helical section have a different lead.

7. The drug delivery device according to claim 6, characterized in that a third section of the groove or slot is provided between the first helical section and the second helical section with the third section having a lead differing from the leads of the first helical section and the second helical section.

8. The drug delivery device according to claim 1 further comprising detents configured to releasably rotationally fix the cartridge holder to the body or the dose setting mechanism.

9. The drug delivery device according to claim 8, characterized in that the detents are provided on the cartridge holder and the body or the dose setting mechanism, respectively.

10. The drug delivery device according to claim 1, characterized in that at least four pairs of the corresponding pairs of ramps are provided on respective end faces of the body and cartridge holder.

11. The drug delivery device according to claim 1, the dose setting mechanism comprising a piston rod and a driver, wherein the driver comprises two driver components which are rotationally coupled to each other during dose setting and dose dispensing and which are rotationally decoupled from each other during resetting of the dose setting mechanism.

12. The drug delivery device according to claim 11, characterized in that a clutch is provided for coupling and decoupling the two driver components, wherein decoupling of the two driver components requires a relative axial movement between the two driver components.

13. The drug delivery device according to claim 12, characterized in that the relative axial movement between the two driver components to effect de-coupling is provided by the axial or helical movement of the piston rod.

14. The drug delivery device according to claim 11, characterized in that a spring is provided biasing the two driver components into a coupled position.

15. The drug delivery device according to claim 11, characterized in that a spring is provided biasing the two driver components to decouple, wherein the cartridge holder causes the two driver components to couple if the cartridge holder is coupled to the body or the dose setting mechanism.

16. The drug delivery device according to claim 1 further comprising a medicament contained in a cartridge.

* * * * *